United States Patent [19]

Roentsch et al.

[11] Patent Number: 5,654,337

[45] Date of Patent: Aug. 5, 1997

[54] TOPICAL FORMULATION FOR LOCAL DELIVERY OF A PHARMACEUTICALLY ACTIVE AGENT

[75] Inventors: Elmer George Roentsch, Stoddard, N.H.; William Scott Snyder, II, 8526 E. Fort Cooper Rd., Inverness, Fla. 34450

[73] Assignee: William Scott Snyder, II, Inverness, Fla.

[21] Appl. No.: 410,459

[22] Filed: Mar. 24, 1995

[51] Int. Cl.$^6$ .............................. A01N 37/10; A61K 31/19
[52] U.S. Cl. ................................................ 514/570; 514/78
[58] Field of Search ........................ 514/570, 577, 514/578, 817, 944, 946, 947, 78; 424/484

[56] References Cited

U.S. PATENT DOCUMENTS

| | | |
|---|---|---|
| 3,154,470 | 10/1964 | Braun et al. |
| 3,957,971 | 5/1976 | Oleniacz. |
| 4,385,049 | 5/1983 | Cuca. |
| 4,794,106 | 12/1988 | Takashima et al. |
| 4,847,069 | 7/1989 | Bissett et al. ........................... 424/47 |
| 5,016,652 | 5/1991 | Rose et al. |
| 5,045,565 | 9/1991 | Gardner et al. ........................ 514/487 |
| 5,093,133 | 3/1992 | Wisniewski et al. |
| 5,210,099 | 5/1993 | Mody et al. |

FOREIGN PATENT DOCUMENTS

| | | |
|---|---|---|
| 2288515 | 5/1976 | France. |
| 4021082 | 1/1992 | Germany. |
| 61-260015 | 11/1986 | Japan. |
| 01242521 | 9/1989 | Japan. |
| 8900077 | 1/1989 | WIPO. |

OTHER PUBLICATIONS

Veys, E.M. (1991) "20 Years' Experience with Ketoprofen" Scan. J. Rheumatol. 90:3–44.

Touitou, E. et al. (1994) "Liposomes as Carriers for Topical and Transdermal Delivery" Journal of Pharmaceutical Sciences 83(9):1189–1203.

Chi, S.-C., H.W. Jun (1990) "Anti-inflammatory Activity of Ketoprofen Gel on Carrageenan-Induced Pau Edema in Rats" Journal of Pharmaceutical Sciences 79(11):974–977.

Chi, S.C., H.W. Jun (1991) "Release Rates of Ketoprofen from Poloxamer Gels in a Membraneless Diffusion Cell" Journal of Pharmaceutical Sciences 803):280–283.

Seth, P.L. (1993) "Percutaneous Absorption of Ibuprofen from Different Formulations" Arzneim.-Forsch./Drug Res. 43(11), Nr. 8:919–921.

Scartazzini, R., P.L. Luisi (1988) "Organogels from Lecithins" J. Phys. Chem. 92:829–833.

Schurtenberger, P. et al. (1990) "Structural and Dynamic Properties of Polymer–like Reverse Micelles" J. Phys. Chem. 94:3695–3701.

Luisi, P.L. et al. (1990) "Colloid Science, Oroganogels from water-in-oil microemulsions" Colloid Polym. Sci. 268:356–374.

Tayar, N.E. et al. (1991) "Percutaneous Penetration of Drugs: A Quantitative Structure–Permeability Relationship Study" Journal of Pharmaceutical Sciences 80(8):744–749.

Willimann, H. et al. (1992) "Lecithin Organogel as Matrix of Transdermal Transport of Drugs" Journal of Pharmaceutical Sciences 81(9):871–874.

*Primary Examiner*—James J. Seidleck
*Assistant Examiner*—Michael A. Williamson
*Attorney, Agent, or Firm*—Saliwanchik, Lloyd & Saliwanchik

[57] ABSTRACT

This invention relates to a composition useful in the delivery of pharmaceutically active agents through the skin. In one embodiment of the invention, the composition is formulated with a non-steroidal anti-inflammatory agent, such as ibuprofen or ketoprofen. Such formulation is rapidly absorbed through the skin to provide local relief from pain. In another embodiment of the invention, the composition is formulated with an antineoplastic agent. Such formulation is rapidly absorbed through the skin to provide local delivery to subcutaneous tumors. The composition is useful for transcutaneous delivery of other pharmaceutically-active compounds.

14 Claims, No Drawings

TOPICAL FORMULATION FOR LOCAL DELIVERY OF A PHARMACEUTICALLY ACTIVE AGENT

BACKGROUND OF THE INVENTION

I. Field of the Invention

This invention relates to a composition useful in the delivery of pharmaceutically active agents through the skin. In one embodiment of the invention, the composition is formulated with a non-steroidal anti-inflammatory agent, such as ibuprofen or ketoprofen; a muscle relaxant, such as cyclobenzaprine; or other active ingredient. Such formulation is rapidly absorbed through the skin to provide local relief from pain, muscle spasms, or other pathological condition. In another embodiment of the invention, the composition is formulated with an antineoplastic or other pharmaceutically-active agent. Such formulation is rapidly absorbed through the skin to provide local delivery to subcutaneous tumors and other subdermal sites in need of treatment.

II. Information Disclosure

There has been much interest in recent years in devising ways to achieve efficient transdermal delivery of pharmaceutically active agents. Dimethyl sulfoxide, DMSO, is an agent which is known to rapidly and efficiently carry dissolved agents across membranes. However, widespread use of this agent has met with considerable resistance, and its use for delivery of pharmaceutical agents is in disfavor. Other agents for achieving percutaneous delivery have been described.

Thus, in U.S. Pat. No. 5,093,133, a method for percutaneous delivery of ibuprofen using a hydroalcoholic gel was described. According to that disclosure, the rate of ibuprofen absorption across the skin was highly pH dependent, dropping from about 1 mg/hour at pHs below about 5.5 to about 0.1 mg/hour at a pH of about 7.0.

U.S. Pat. No. 5,210,099 described an analgesic cream which, through maintaining a pH of 4 to 7.2 such that the ibuprofen was suspended in substantially solid crystalline form, provided skin penetration at a rate of about 39.8 µg/cm²/hour. The compositions into which the ibuprofen was formulated were conventional in the art, such as the water-in-oil emulsion compositions of U.S. Pat. Nos. 3,154,470; 4,385,049; and 4,794,106.

U.S. Pat. No. 3,957,971 described liposomes having (i) a matrix of a ternary lipid mixture of lecithin, dicetyl phosphate, and a sterol, and (ii) an aqueous solution of a humectant such as glycerol, urea, sodium pyroglutamate, ornithine, or Spier-Pascher water solubles inside the liposome. The liposomes were described as a skin moisturizer. There is no disclosure of including a pharmaceutically active compound for transdermal delivery.

U.S. Pat. No. 5,016,652 describes a patch for transdermal delivery of nicotine to reduce cigarette smoking. The patch optionally includes a skin penetration enhancer such as DMSO, sodium lauryl sulfate, Azone, or a mixture of propylene glycol and oleic acid. The patent also references several other transdermal drug delivery patch patents.

In Willimann et al., 1992, a composition comprising a "lecithin organogel" was described wherein small amounts of water were added to a solution of lecithin in an organic solvent to induce gelation. Transport rates of scopolamine and broxaterol across human skin samples in a Franz diffusion cell were reported to be about ten-fold higher in the lecithin organogel than in aqueous solution of these drugs at the same concentration. Transdermal passage of these compounds in the solution form of the mixture (i.e., prior to addition of water to form a gel) were noted to be the same as when measured in the gel form. Successful transdermal delivery of amino acids and peptides was also noted. In that report, the ratio of water to lecithin was strongly emphasized as a critical feature. Thus, a parameter called $w_o=[H_2O]/[lecithin]$ was described, and values of between 0–12 for this concentration ratio were described. The gelation was described entirely as a function of this parameter, and the incorporation of urea or a surfactant was neither disclosed nor suggested.

Veys, 1991, reviewed experience with ketoprofen which is a potent non-steroidal anti-inflammatory drug (NSAID). Topical delivery of the drug in the form of a ketoprofen gel was discussed and it was shown that absorption and elimination half-lives were 3.2±2.4 hours and 27.7±18.0 hours respectively.

Chi and Jun, 1990 & 1991, disclosed ketoprofen-pluronic F-127 formulations for topical delivery of ketoprofen.

In May 24–30, 1994, at the Jerusalem Conference on Pharmaceutical Sciences and Clinical Pharmacology, the state of the art in transdermal delivery of pharmaceutically active agents using liposomes was reviewed.

Tayar et al., 1991, provide a study on the theoretical aspects of percutaneous penetration of drugs.

Seth, 1993, describes ibuprofen absorption from three different formulations.

Luisi et al., 1990, provides a review of a new class of gels called lecithin gels. They note that gelation of lecithin (50–200 mM) in an organic solvent, occurs upon addition of between 1 to 12 moles of water per mole of lecithin, depending on which of the 50 different organic solvents tested is used to dissolve the lecithin. The physico-chemical properties of these organogels are discussed, and a model, which attempts to account for the peculiar viscosity characteristics of the gels, is proposed.

Schurtenberger et al., 1990, and Scartazzini et al., 1988, were authored by the same group as the above-discussed Luisi et al. review, which largely summarized the content of these papers.

BRIEF SUMMARY OF THE INVENTION

This invention relates to a composition useful in the delivery of pharmaceutically active agents through the skin. The composition comprises a mixture of a polar lipid such as lecithin or phosphatidylcholine, a biocompatible organic solvent such as an isopropyl palmitate or isopropyl myristate ester, water, urea, and a biocompatible surfactant such as docusate sodium, docusate sodium benzoate, or ibuprofen, at a pH of between about 6.0 and 8.0. In addition, the composition may optionally include cholesterol, or a preservative such as benzyl alcohol. Upon formulation of this composition with the pharmaceutically active agent, and, upon brining the pH to the desired range, the formulation thickens and forms a gel for topical administration. In one embodiment of the invention, the composition is formulated with a non-steroidal anti-inflammatory agent, such as ibuprofen or ketoprofen. Such formulation is rapidly absorbed through the skin and provides local relief from pain. In another embodiment of the invention, the composition is formulated with an antineoplastic or other pharmaceutically-active agent. Such formulation is rapidly absorbed through the skin to provide local delivery to subcutaneous tumors and other subdermal sites in need of treatment. Several other formulations are also disclosed, such as those active as a muscle relaxant by virtue of an included active compound such as cyclobenzaprine.

DETAILED DISCLOSURE OF THE INVENTION

This invention relates to a composition useful in the delivery of pharmaceutically active agents through the skin. The composition comprises a mixture of a polar lipid such as lecithin or phosphatidylcholine, a biocompatible organic solvent such as isopropyl palmitate or isopropyl myristate esters, a surfactant, water, and urea, at a pH of between about 6.0 and 8.0 and preferably between 6.0 and 7.0. In addition, the composition may optionally include cholesterol or a preservative such as benzyl alcohol.

Preferably, the lecithin or phosphatidylcholine is of a high quality, pharmaceutical grade. Appropriate lecithin and phosphatidylcholine maybe obtained as commercially available soya lecithin or soya phosphatidylcholine. Preferably, soya lecithin is used in the composition of this invention.

The biocompatible organic solvent may be any non-toxic solvent in which the polar lipid, the pharmaceutically active compound and urea are soluble, and which assists as a solubilizing vehicle for carrying pharmaceutically active compounds across the skin of a mammal. Acceptable esters for this purpose include, but are not limited to isopropyl esters. Preferably, the ester is isopropyl myristate or isopropyl palmitate, with isopropyl myristate being particularly preferred.

In preparing the composition of this invention, the polar lipid is dissolved in the organic solvent at mass ratios anywhere from 5:1 to 1:5. Preferably, the polar lipid and organic solvent are mixed in even mass ratios. Thus, in one embodiment of the invention, soya lecithin and isopropyl myristate are mixed in equal mass ratios and mixed until the lecithin is evenly distributed in the isopropyl myristate. This mixture, called lecithin organogel (L.O.), is stable and may be used even after prolonged storage without loss of activity.

Once the solvent-polar lipid mixture is thoroughly dispersed, the pharmaceutically active compound may be added and dissolved. This is most easily achieved by heating an aliquot of the solvent-polar lipid mixture and adding, on a mass basis, an amount of active compound equal to about 0.01 to 30% of the mass of the solvent-polar lipid and mixing until completely dissolved. Thus, for example, about 1–20 grams of ibuprofen (preferably the S-isomer) or ketoprofen in a powdered form is added to about 100 grams of heated 1:1 soya lecithin:isopropyl myristate and allowed to dissolve with stirring. The pharmaceutically active compound may be an analgesic such as salicylic acid or the non-steroidal anti-inflammatory agents ibuprofen and ketoprofen. It may be a topical anaesthetic such as lidocaine. It may be a steroidal anti-inflammatory, such as cortisone. It may be an anti-neoplastic agent such as doxorubicin. It may be a peptide, protein, or hormone, such as platelet factor 4 which exhibits angiostatic activity. It may be a substance P antagonist such as capsaicin. It may be a muscle relaxant such as cyclobenzaprine. It may be an antifungal compound such as FLUCONAZOLE®. It may be an anti-inflammatory analgesic such as diclofenac sodium. It may be an anti-anginal compound such as nifedipine. It may be a cellulite reducer such as theophylline or aminophylline. In the event of using a proteinaceous pharmaceutically active compound, one must avoid adding the protein to a too-warm solution of solvent-polar lipid mixture as this might denature the protein if it is not thermostable.

Depending on the nature of the pharmaceutically active compound and the desired characteristics of the final formulation, a surfactant is included in the formulation at a concentration of between about 1–20% of the final composition mass. In the formulation including ibuprofen, we have found that ibuprofen exhibits surfactant properties, and addition of another surfactant is therefore not needed. In the case of ketoprofen, on the other hand, addition of a surfactant is beneficial. Preferably, the surfactant is one which is compatible with administration in vivo without elicitation of undesirable side effects. One such surfactant which has found wide-spread use in the formulation of stool softeners is docusate sodium and its more water soluble form, docusate sodium benzoate. Other appropriate ionic or non-ionic surfactants, such as polysorbate 80 or Tween 80, may naturally be used.

Either before or after addition of the pharmaceutically active compound, an mount of urea, preferably as an aqueous solution, is added to the solvent-polar lipid mixture. The urea is added so that the urea concentration will be between about 5% and 20% by mass of the final composition mass. Thus, using a 20% aqueous solution of urea, about 10 grams is added to about 100 grams of the solvent-polar lipid mixture with dissolved pharmaceutically active compound. In some instances, the pharmaceutically active agent will more readily dissolve if added after addition of the urea, and in other instances before the addition of urea. In any event, this is a choice easily made by those skilled in the art depending on the particular formulation being prepared and the solubility characteristics of the particular pharmaceutically active compound being solubilized. In the case of ibuprofen and a mixture of soys lecithin-isopropyl myristate, the ibuprofen is preferably added before addition of the urea. If the pharmaceutically active agent is a protein, it will be necessary to test the retention of biological activity of the protein upon exposure to the particular urea concentration used in this formulation as the chaotropic properties of urea are known to denature some proteins. Such a determination is easily conducted by one of ordinary skill in the art.

Upon formulation of the above described composition with the pharmaceutically active agent, the pH is adjusted to about a pH of 6.0 to 7.0. This is easily accomplished, for example, by addition of aqueous sodium hydroxide, as the compositions initially tend to have an acid pH. Naturally, if the pharmaceutically active agent tends to produce very alkaline solutions, addition of acid to reduce the pH would be desirable. This is easily accomplished by addition of citric acid or a biological buffer such as sodium carbonate or triethanolamine, as in trolamine salicylate. Once the composition reaches a pH in the range of about 6.0 to 7.0, the formulation thickens and forms a gel for topical administration.

In one embodiment of the invention, the composition is formulated with a non-steroidal anti-inflammatory agent, such as ibuprofen or ketoprofen. Such formulation is rapidly absorbed through the skin and provides local relief from pain. In another embodiment of the invention, the composition is formulated with an antineoplastic agent. Such formulation is rapidly absorbed through the skin to provide local delivery to subcutaneous tumors.

For ease of preparation, it is convenient to prepare a first gel composition, named speed-gel herein, which can be used to add to other components in the formulation of a final composition for topical administration. There are several possible formulations of the speed-gel. For example, a speed-gel may be prepared by mixing lecithin organogel (L.O.), as a 1:1 (m/m) mixture of lecithin and isopropyl myristate, with LID oil (a 1:1 [m/m] mixture of L.O. and docusate sodium), dissolving additional docusate sodium powder into this mixture, and then adding aqueous urea.

In one embodiment of the speed-gel formulation, the final concentrations are: L.O.=25%; docusate sodium=15%; urea=10%; and water=50%. These ratios may easily be varied such that the final amounts of each component are as follows: L.O.=20–30%; docusate sodium or another surfactant=10–20%; urea=5–20%; and water=30–60%. The speed-gel may then be added to solubilized active ingredients and other excipients which may be useful in solubilizing the active ingredient, such as DMSO, peppermint oil, glycerin, and/or polyethylene glycol. An homogenous mixture is then made by carefully blending the various components.

In experiments with the ingredients in the speed-gel, we tested whether a clear, amber colored, homogenous gel solution with reproducible and pleasant consistency could be made by altering the order and ratios of its constituents. Surprisingly, we found that all of the ingredients, namely lecithin organogel (L.O.), surfactant, aqueous urea, and a pH of between about 6.0 and 8.0, are necessary to achieve the desired gel. In addition, it is preferable that the components be compounded in the order: L.O., then surfactant, then aqueous urea, then pH adjustment. Addition of a lipophilic pharmaceutically active ingredient is preferably achieved by first solubilizing the active ingredient in the L.O. or by first solubilizing the ingredient in a minimal amount of DMSO or peppermint oil or like solvent, and then mixing it with the. L.O. for compounding with the other components. Addition of an ionic or otherwise water-soluble active agent is achieved by either adding the agent to the L.O. or to the aqueous urea phase. Varying the approach to mixing the gel slightly but maintaining the integrity of the appropriate ratios of the components and the order of addition, still allows for the formation of an acceptable gel. Alteration of the ratios beyond the limits described herein, may interfere with product consistency and gel formation. Thus, for example, when urea is eliminated from the formulation, a creamy colored and textured mixture is achieved which did not form a pleasant gel between pH 4.8 to pH 12.5. Likewise, when no surfactant is added, substituting an equal mass of L.O. in its place, a creamy and very viscous mixture was attained. Subsequent addition of docusate sodium did not rectify the unpleasant character of this mixture. By routine experimentation, using each of the critical elements of this composition, those skilled in the art will be able to make specific gels of essentially any active ingredient or combination thereof for a wide variety of typical applications.

Once the formulations described above have been prepared, use of the formulations is a simple matter of applying the formulation to affected areas where transdermal delivery of the pharmaceutically active agent is desired. Thus, in the case of arthritis, formulations containing ibuprofen are rubbed over the affected area such as the joints of the hands. Treatment is repeated as pain symptoms reappear. In multiple applications of formulations prepared according to this invention prescribed by doctors around the country, doctors and patients have reported almost immediate reduction of arthritis associated pain.

In another aspect of this invention, a non-steroidal anti-inflammatory compound is formulated for delivery to hemorrhoidal tissue. As with treatments of arthritis associated pain, in multiple treatments, doctors and patients across the country have confirmed almost immediate reduction in hemorrhoidal associated pain. Thus, the gel of the instant invention is advantageously formulated in a suppository form or simply applied directly to the surface of affected tissues.

In other applications, such agents as anti-neoplastic drugs such as doxorubicin, or biologically active proteins, are formulated and directly applied to areas where local delivery of these active compounds is needed.

In another aspect of this invention, topical application of a hair growth enhancer is achieved by incorporation into the composition of an agent such as minoxidil. A concentration of about 0.1% to about 10%, and preferably about 2% minoxidil in the composition of this invention is desirable. In addition, a composition comprising an inhibitor of testosterone 5-α reductase, such as finasteride, could be used to advantage for this and other purposes. Finally, compositions comprising a mixture of minoxidil and a testosterone 5-α reductase inhibitor would be very beneficial for inducing increased hair growth. Because of the very good skin penetration achieved using the composition of this invention, lower doses of minoxidil could be delivered than are currently used in such formulations as ROGAINE®, which is 2% minoxidil in a solution of alcohol 60% v/v, propylene glycol and water.

In another aspect of this invention, a composition comprising an antibacterial agent is prepared, for example, by inclusion of bacitracin or another appropriate antibiotic. This allows for penetration of the antibacterial agent to sites of infection induced by puncture wounds.

In general, compositions of this invention are provided at a concentration of between about 0.01% to 30% by weight of active compound. In addition, compositions comprising more than one active ingredient are within the scope of this invention and could be administered to a recipient in need of more than a single active treatment at one localized spot. Thus, for example, a composition comprising an analgesic and an antifungal would both provide relief from acute pain and will provide long-term relief once the fungal infection has been completely eliminated.

It is contemplated that the compositions of this invention are applied topically as frequently as required as long as local reactions or toxicity due to the active ingredient do not become a problem. Thus, for example, a more rigorously monitored regimen of application may be required when an anti-neoplastic compound is being administered than when a readily metabolized non-toxic compound such as ketoprofen is administered. In the latter case, it would be acceptable for a person in need of such treatment to topically apply the composition as frequently as needed to achieve relief from local pain or inflammation.

While the foregoing description generally describes how to make and use the compositions and formulations of this invention, the following examples are provided to more specifically point out how to practice the invention. However, it should be clearly understood that the scope of this invention, as defined by the claims appended hereto, is not to be limited to the specifics of the following examples. Further, it should be understood that, in the specific compositions described and claimed, the percentages of active and other ingredients could be within at least a 10% different amount while still achieving an objective equivalent to the specifically disclosed compositions.

EXAMPLE 1—Preparation of Speed-Gel

|  |  |
| --- | --- |
|  | 360 gm |
| LID Oil* | 36 gm |
| Lecithin organogel** (L.O.) | 72 gm |

|  |  |
|---|---|
|  | 360 gm |
| Docusate sodium powder | 36 gm |
| Urea | 36 gm |
| Distilled water | 180 ml |

*LID oil is a 1:1 mixture of lecithin organogel:docusate sodium on a mass basis.
**L.O. is a 1:1 mixture of lecithin and isopropyl myristate.

1. The LID was added to L.O. and heated.
2. Docusate sodium powder was added, and the mixture was stirred until smooth.
3. Urea was added to water, heated, and added to step 2 with stirring.
4. pH was adjusted to between 6.5 to 6.9.

Speed-gel may just as easily be prepared as follows:

|  |  |
|---|---|
|  | 100 gm |
| L.O. | 25 gm |
| Docusate sodium benzoate powder | 15 gm |
| Urea | 10 gm |
| Distilled water | 50 gm |

The L.O. was heated and the docusate sodium benzoate powder was stirred into the heated L.O. until a smooth solution is prepared. The water was heated and the urea was dissolved into the water, and the urea solution was then thoroughly mixed with the docusate sodium containing solution of L.O. The result was a consistent, transparent, amber colored gel with a pH of about 6.0.

Yet another way of making speed-gel is as follows:

|  |  |
|---|---|
|  | 100 gm |
| L.O. | 10 gm |
| LID | 30 gm |
| Urea | 10 gm |
| Distilled water | 50 gm |

The LID and L.O. were mixed well and a heated solution of water and the urea was prepared and added to the LID-L.O. solution. The result was a consistent, transparent, amber colored gel with a pH of about 6.0.

EXAMPLE 2—Preparation of Nifedipine Composition

|  |  |
|---|---|
|  | #30 gm |
| Nifedipine | 0.3 gm |
| Dimethyl sulfoxide (DMSO) | 43 drops |
| Polysorbate 80 | 2 ml |
| Speed-gel | qs to 30 gm |

1. Nifedipine was dissolved in the DMSO with trituration in mortar.
2. 2 ml polysorbate 80 was added with trituration to thicken.
3. qs to 30 gm with new speed gel.

The composition was dispensed into a 1 oz. cc syringe with Luer tip cap and stored in a light-resistant bag.

EXAMPLE 3—Preparation of 5% Ketoprofen Composition

|  |  |
|---|---|
|  | 30 gm |
| Ketoprofen | 1.5 gm |
| Lecithin organogel | 5 gm |
| Speed-gel | qs to 30 gm |

The L.O. was heated and ketoprofen added and stirred until a consistent, fairly thin creamy-colored mixture was achieved. Speed-gel was then added, and the composition was treated to remove bubbles. The pH was adjusted to 6.8 with 30% NaOH. At about pH 6.0, the solution thickened, became clear, and from this point to pH 6.8, it was a thick, amber-colored, homogenous gel.

EXAMPLE 4—Preparation of Another 5% Ketoprofen Composition

|  |  |
|---|---|
|  | 30 gm |
| Ketoprofen | 1.5 gm |
| Tween 80 | 3.0 gm |
| Speed-gel | qs to 30 gm |

Ketoprofen was added to Tween 80 and heated until a clear solution was achieved, then speed-gel was added.

EXAMPLE 5—Preparation of Another 5% Ketoprofen Composition

|  |  |
|---|---|
|  | 30 gm |
| Ketoprofen | 1.5 gm |
| Lecithin organogel | 7 gm |
| Speed-gel | 22 gm |

1. The ketoprofen was dissolved in lecithin organogel using moderate heat.
2. Speed-gel was added and the mixture was heated in a microwave to a clear thin gel.
3. The mixture was then set on a hot plate with stirring.
4. 30% NaOH was then added to bring the pH to 5.8–6.8 to form a gel.

EXAMPLE 6—Preparation of 5% Ketoprofen, 2% Lidocaine Gel, Keto-Lido 5-2

|  |  |
|---|---|
|  | 30 gm |
| Ketoprofen | 1.5 gm |
| Lidocaine base | 0.6 gm |
| Lecithin organogel | to wet |
| Speed-gel | qs to 30 gm |

1. The ketoprofen and lidocaine were triturated to a fine powder.
2. The speed-gel was heated and added to the powders with stirring.
3. A few drops of lecithin organogel were added to the mixture to thicken.
4. The composition was dispensed into a jar for later use.

EXAMPLE 7—Preparation of a Ketoprofen (5%), Lidocaine (2%), Cyclobenzaprine (0.5%) Gel

| | 60 gm |
|---|---|
| Cyclobenzaprine | 0.3 gm |
| Polysorbate 80 | to wet |
| Keto-Lido 5-2 (from Example 6) | qs to 60 gm |

1. The cyclobenzaprine was moistened with polysorbate.
2. The mixture was brought to final weight by trituration with Keto-Lido 5-2 compound of Example 6.

EXAMPLE 8—Preparation of Ketoprofen (5%), Lidocaine (2%), Cyclobenzaprine (0.5%) Gel

| | 60 gm |
|---|---|
| Ketoprofen | 3 gm |
| Lidocaine base | 1.2 gm |
| Cyclobenzaprine | 0.3 gm |
| L.O. | to wet |
| Speed-gel | qs to 60 gm |

1. The ketoprofen, lidocaine and cyclobenzaprine were triturated to a fine powder.
2. The speed-gel was heated and added to the powders with stirring.
3. A few drops of lecithin organogel were added to the mixture to thicken.
4. The formulation was dispensed into a jar for later use.

EXAMPLE 9—Ketoprofen 10% Gel

| | 60 gm |
|---|---|
| Ketoprofen | 6 gm |
| L.O. | 7 gm |
| Speed-gel | 44 gm |
| LID oil or polysorbate 80 | 2-3 ml to thicken |

1. L.O. was added to the ketoprofen and stirred to a smooth paste.
2. Speed-gel was added and stirred to smooth paste and heated until clear.
3. 2-3 ml of LID oil was then added.
4. The pH and thickness were then adjusted by titrating the pH to 5.9-6.8 with 30% NaOH.

EXAMPLE 10—Ketoprofen 10%, Cyclobenzaprine 1% Gel

| | 30 gm |
|---|---|
| Ketoprofen | 3 gm |
| Cyclobenzaprine | 0.3 gm |
| Speed-gel | qs to 30 gm |

1. The powders were triturated until fine.
2. The speed-gel was added and mixed until smooth.

EXAMPLE 11—20% Ibuprofen Gel

A speed-gel containing ibuprofen was prepared without the need to add any additional surfactant because the ibuprofen itself acts as a surfactant. This formulation was prepared as follows:

| | 100 gm |
|---|---|
| Ibuprofen | 20 gm |
| L.O. | 25 gm |
| Urea | 10 gm |
| Water | 36 gm |
| Benzyl Alcohol | 1 ml |
| 30% NaOH | 5 ml |

These reagents were mixed in the order listed above and brought to a pH of about 6.8. The gel has a pleasant amber color and light, even consistency.

EXAMPLE 12—Trolamine Salicylate 10% Speed-Gel

The following analgesic topical solution was prepared:

| | 30 gm |
|---|---|
| Salicylic acid | 1.5 gm |
| Trolamine | 1.5 gm |
| Ethyl Alcohol (95%) | 1.0 ml |
| Tween 80 | 1 gm |
| Speed-Gel | 16 gm |
| L.O. | 9 gm |

1. The salicylic acid, trolamine, alcohol and tween were combined, triturated and heated to form a clear solution.
2. The speed-gel was added.
3. The L.O. was added and the gel formed was dispensed into a container for later use.

EXAMPLE 13—Aminophylline 2% Speed-Gel

The following cream is prepared to reduce cellulite by transport of aminophylline (theophylline ethylenediamine, 2:1; theophylline is 3,7-dihydro-1,3-dimethyl-1H-purine-2, 6-dione) across the skin and into adipose tissue. Transdermal delivery of this active agent across the skin is known to achieve cellulite reduction as described in *Clinical Therapeutics* 9(No. 6):663–671, 1987.

| aminophylline | 2 gm |
|---|---|
| L.O. | 10 gm |
| speed-gel | qs to 100 gm |

The aminophylline is dissolved in heated L.O. and then mixed with the speed-gel to form a consistent and easily applied gel.

EXAMPLE 14—Capsaicin Speed-Gel

A speed gel for relief of, for example, postherpetic neuralgia, is prepared as a 0.025 to 0.075% gel of capsaicin oleoresin:

| Capsaicin | 0.025 gm |
|---|---|
| L.O. | 1 gm |
| Speed-gel | qs to 100 gm |

The capsaicin is wetted with the L.O. and then mixed thoroughly with the speed gel. This gel is applied topically, as needed, to relieve local pain in the aftermath of shingles.

It should be understood that the examples and embodiments described herein are for illustrative purposes only and

References Cited

U.S. Pat. Nos.
5,093,133
5,210,099
3,154,470
4,385,049
4,794,106
3,957,971
5,016,652

Other References

Chi, S. C., H. W. Jun (1990) *J. Pharmaceutical Sci.* 79:974–977.

Chi, S. C., H. W. Jun (1991) *J. Pharmaceutical Sci.* 80:280–283.

Luisi et al. (1990) *Colloid Polym. Sci.* 268:356–374.

May 24–30, 1994, at the Jerusalem Conference on Pharmaceutical Sciences and Clinical Pharmacology (see *J. Pharmaceutical Sciences* 83:1189–1203, September 1994).

Schurtenberger et al. (1990) *J. Phys. Chem.* 94:3695–3701.

Scartazzini et al. (1988) *J. Phys. Chem.* 92:829–833.

Seth, P. L. (1993) *Arzneim-Forsch/Drug Res.* 43(11):919–921.

Tayar et al. (1991) *J. Pharm. Sci.* 80:744–749.

Veys, E. M. (1991) *Scand. J. Rheumatol.* Suppl. 90:3–44.

Willimann, H. et al. (1992) *J. Pharmaceutical Sci.* 81:871–874.

We claim:

1. A composition for the delivery of a pharmaceutically active substance through the skin of a mammal which comprises a biocompatible organic solvent, a polar lipid, a surfactant, water, urea and the pharmaceutically active substance to be delivered, at a pH of about 6.0 to 8.0, wherein the polar lipid is lecithin or phosphatidylcholine, the biocompatible organic solvent is an isopropyl ester, selected from the group consisting of isopropyl myristate and isopropyl palmitate, and the urea is present at a concentration of about 5 to 20% by mass of the final composition.

2. The composition, according to claim 1, wherein the polar lipid is lecithin.

3. The composition, according to claim 2, wherein the surfactant is selected from the group consisting of docusate sodium, docusate sodium benzoate, docusate calcium, tween 80, polysorbate 80, and ibuprofen.

4. The composition, according to claim 1, wherein the pharmaceutically active substance is an analgesic, an antiinflammatory, a biologically active protein, a cellulite reducer, a substance P antagonist, or an antineoplastic compound.

5. The composition, according to claim 4, wherein the pharmaceutically active substance is a non-steroidal antiinflammatory agent.

6. The composition, according to claim 5, wherein the pharmaceutically active substance is ibuprofen or ketoprofen.

7. A composition comprising, as a percentage of the mass of the final composition:

(a) Lecithin 10–30%;

(b) isopropyl myristate 10–30%;

(c) urea 5–20%;

(d) water 30–60%;

(e) a surfactant 10–20%.

8. The composition, according to claim 7, further comprising about 1% nifedipine.

9. The composition, according to claim 7, further comprising about 5–10% ketoprofen, or 5–20% ibuprofen.

10. The composition, according to claim 7, further comprising about 2% lidocaine, 0.025–0.075% capsaicin P or 2% aminophylline.

11. The composition, according to claim 10, further comprising about 1% cyclobenzaprine.

12. A method of making a composition for transcutaneous delivery of a pharmaceutically active substance which comprises:

(a) dissolving a polar lipid in an about equal mass of biocompatible organic solvent;

(b) adding a surfactant to the composition of step (a) to a concentration of about 10% to about 20%;

(c) dissolving a pharmaceutically active compound in the solvent-polar lipid, surfactant mixture of step (b) to a concentration of about 0.01% to about 30%;

(d) adding aqueous urea to a concentration of about 5% to about 20%; and (e) adjusting the pH to between about 6.0 to 8.0.

13. A composition prepared according to the method of claim 12.

14. A composition consisting essentially of:

lecithin 10–15%;

isopropyl myristate 10–15%;

docusate sodium 10–20%;

urea 5–15%; and water 25–60%;

and at least one pharmaceutically active ingredient present at between 0.01–30%, at a pH of between about 6.0 to 7.0.

* * * * *